United States Patent
Rothe et al.

(10) Patent No.: US 10,365,283 B2
(45) Date of Patent: Jul. 30, 2019

(54) ACTIVATED HER3 AS A MARKER FOR PREDICTING THERAPEUTIC EFFICACY

(71) Applicant: U3 PHARMA GMBH, Martinsried (DE)

(72) Inventors: Mike Rothe, Krailling (DE); Martin Treder, Martinsried (DE)

(73) Assignee: Daiichi Sankyo Europe GmbH, Munich (DE)

( * ) Notice: Subject to any disclaimer, the term of this patent is extended or adjusted under 35 U.S.C. 154(b) by 0 days.

(21) Appl. No.: 15/047,041

(22) Filed: Feb. 18, 2016

(65) Prior Publication Data

US 2016/0161491 A1    Jun. 9, 2016

Related U.S. Application Data

(62) Division of application No. 12/516,682, filed as application No. PCT/EP2007/010335 on Nov. 28, 2007, now abandoned.

(60) Provisional application No. 60/861,243, filed on Nov. 28, 2006.

(30) Foreign Application Priority Data

Nov. 28, 2006   (EP) .................................. 06024658

(51) Int. Cl.
| | | |
|---|---|---|
| G01N 33/574 | (2006.01) | |
| C07K 16/28 | (2006.01) | |
| C07K 16/32 | (2006.01) | |
| A61K 39/395 | (2006.01) | |
| G01N 33/53 | (2006.01) | |
| A61K 39/00 | (2006.01) | |

(52) U.S. Cl.
CPC ..... *G01N 33/5748* (2013.01); *C07K 16/2863* (2013.01); *C07K 16/32* (2013.01); *G01N 33/574* (2013.01); *G01N 33/57407* (2013.01); *G01N 33/57492* (2013.01); *A61K 39/395* (2013.01); *A61K 2039/505* (2013.01); *C07K 2317/76* (2013.01); *G01N 2333/71* (2013.01); *G01N 2333/91205* (2013.01); *G01N 2440/14* (2013.01); *G01N 2800/205* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,480,968 A | | 1/1996 | Kraus et al. |
| 5,804,396 A | * | 9/1998 | Plowman .................. C12Q 1/48 435/7.2 |
| 6,277,640 B1 | | 8/2001 | Bennett et al. |
| 7,125,680 B2 | * | 10/2006 | Singer .................... C07K 14/71 435/7.1 |
| 8,771,695 B2 | | 7/2014 | Rothe et al. |
| 2002/0110841 A1 | | 8/2002 | Kufe |
| 2004/0001833 A1 | | 1/2004 | Agus |
| 2004/0018528 A1 | * | 1/2004 | Morimoto .............. C12Q 1/485 435/6.14 |
| 2004/0197332 A1 | | 10/2004 | Ullrich et al. |
| 2006/0204505 A1 | | 9/2006 | Sliwkowski et al. |
| 2006/0204966 A1 | | 9/2006 | Spector et al. |

FOREIGN PATENT DOCUMENTS

| | | |
|---|---|---|
| WO | 9735885 A1 | 10/1997 |
| WO | 03013602 A1 | 2/2003 |
| WO | 2005049829 A | 6/2005 |
| WO | 2005117553 A | 12/2005 |
| WO | 2006063042 A | 6/2006 |

OTHER PUBLICATIONS

Gordon et al., "Clinical Activity of Pertuzumab (rhuMAb 2C4), a HER Dimerization Inhibitor, in Advanced Ovarian Cancer; Potential Predictive Relationship with Tumor HER 2 Activation Status", Journal of Clinicial Oncology, vol. 24, No. 26, Sep. 10, 2006.
Scartozzi et al., "The Role of HER-3 Expression in the Prediction of Clinical Outcome for Advanced Colorectal Cancer Patients Receiving Irinotecan and Cetuximab", The Oncologist, 2011; 16; pp. 53-60.
Notice of Opposition dated Oct. 9, 2015 in the corresponding EP application No. 07 846 863.4 (U.S. Pat. No. 2 097 754), 32 pgs.
Phospho-HER3/ErbB3 (Tyr1289) (21D3) Rabbit mAb, Cell Signaling Technology, Product Data Sheet, Sep. 17, 2013, 2 pgs.
Phospho-HER3/ErbB3 (Tyr1222) (50C2) Rabbit mAb, Cell Signaling Technology, Product Data Sheet, Jul. 20, 2010, 3 pgs.
Office Action cited in a Japanese Patent Application No. 2009-538639 dated Feb. 12, 2014, 18 pp. 12516.
Extended European Search Report issued for EP 12 176 507.7, a divisional of EP 07 846 863.4, dated Oct. 1, 2012, 10 pages.
Bono et al., "The ErbB receptor family: a therapeutic target for cancer", Trends in Molecular Medicine, vol. 8, No. 4, Suppl, 2002, pp. S19-S26.
Kakiuchi et al., "Prediction of sensitivity of advanced non-small cell lung cancers to gefitinib (Iressa, ZD1839)", Human Molecular Genetics, vol. 13, No. 24, Dec. 15, 2004, pp. 3029-3043.
Fujimoto et al., Cancer Research 2005, 65(24):11478-85.
Yi et al., Modem Pathology, 1997, 10(2): 142-8.
Mass, Int. J. Radiation Oncology Biol. Phys. 2004, 58(3):932-940.
Kim et al., Breast Cancer Research, 2005, 7:R4708-R719.

* cited by examiner

*Primary Examiner* — Hong Sang
(74) *Attorney, Agent, or Firm* — Rothwell, Figg, Ernst & Manbeck, P.C.

(57) ABSTRACT

The present invention provides methods for the determination of the activation level of Receptor Tyrosine kinases, e.g. phosporylated HER3, for the selection of patients for disease treatment. Methods are also provided for the evaluation of the biological and pharmacodynamic effects of an active substance and/or its efficacy in disease treatment, utilizing a tissue sample from a test subject, for example tumor material or normal tissue such as skin or hair follicle. Further, methods for the treatment of HER receptor-associated diseases are disclosed.

9 Claims, 20 Drawing Sheets

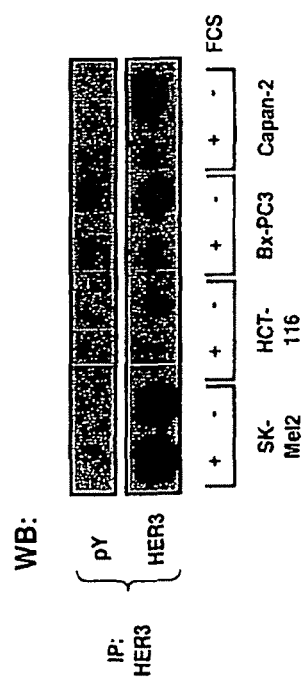

Fig. 2a

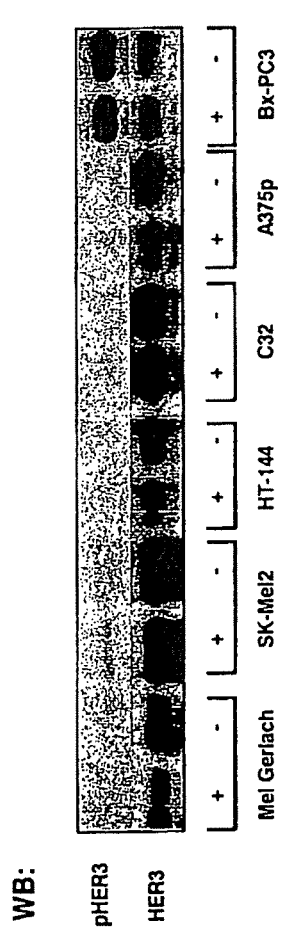

Fig. 3

| Indication | # cell lines | HER3 | pHER3 | % pHER3/total |
|---|---|---|---|---|
| Breast | 18 | 15 | 12 | 66,7 |
| NSCLC | 9 | 8 | 7 | 77,8 |
| Colon | 5 | 5 | 5 | 100 |
| gastric | 7 | 7 | 5 | 71,4 |
| melanoma | 5 | 5 | 2 | 40 |
| pancreas | 5 | 3 | 3 | 60 |
| prostate | 7 | 6 | 5 | 71 |
| Total | 56 | 49 | 39 | 69,6 |

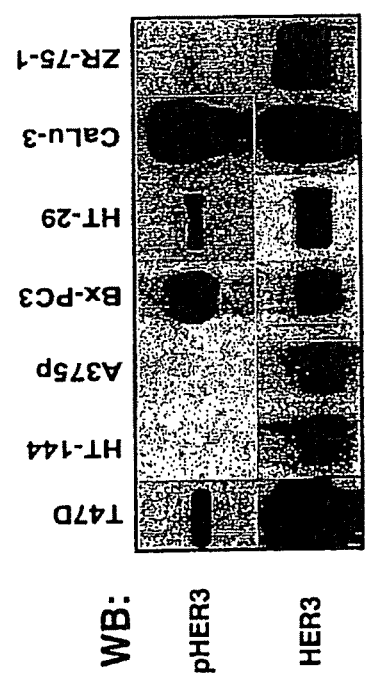

Fig. 4b

| | T47D (breast) | HT-144 (melanoma) | A375p (melanoma) | Bx-PC3 (pancreas) | HT-29 (colon) | CaLu-3 (NSCLC) | ZR-75-1 (breast) |
|---|---|---|---|---|---|---|---|
| pHER3 | Yes | No | No | Yes | Yes | Yes | Yes/No |
| *In vivo* Efficacy | Yes | No | No | Yes | Yes | Yes | No |

ACTIVATED HER3 AS A MARKER FOR PREDICTING THERAPEUTIC EFFICACY

CROSS REFERENCE TO RELATED APPLICATION

This application is a divisional of U.S. Ser. No. 12/516,682 filed May 28, 2009, abandoned, which is a 35 U.S.C. 371 National Phase Entry Application from PCT/EP2007/010335, filed Nov. 28, 2007, which claims the benefit of European Patent Application No. 06 024 658.4 filed on Nov. 28, 2006, which claims the benefit of U.S. Provisional Application No. 60/861,243 filed Nov. 28, 2006, the disclosures of which are incorporated herein in their entirety by reference.

DESCRIPTION

The present invention provides methods for the determination of the activation level of Receptor Tyrosine kinases, e.g. phosporylated HER3, for the selection of patients for disease treatment. Methods are also provided for the evaluation of the biological and pharmacodynamic effects of an active substance and/or its efficacy in disease treatment, utilizing a tissue sample from a test subject, for example tumor material or normal tissue such as skin or hair follicle. Further, methods for the treatment of HER receptor-associated diseases are disclosed.

The human epidermal growth factor receptor 3 (HER3, also known as ErbB3) is a receptor protein tyrosine kinase and belongs to the epidermal growth factor receptor (EGFR) subfamily of receptor protein tyrosine kinases, which also includes HER1 (also known as EGFR), HER2, and HER4 (Plowman et al., Proc. Natl. Acad. Sci. U.S.A. 87 (1990), 4905-4909; Kraus et al., Proc. Natl. Acad. Sci. 86 (1989), 9193-9197; and Kraus et al., Proc. Natl. Acad. Sci. U.S.A. 90 (1993), 2900-2904).

HER3 has been found to be overexpressed in several types of cancer such as breast, gastrointestinal and pancreatic cancers. Interestingly a correlation between the expression of HER2/HER3 and the progression from a non-invasive to an invasive stage has been shown (Alimandi et al., Oncogene 10,181 3-1 821; deFazio et al., Cancer 87, 487-498; Naidu et al., Br. J. Cancer 78, 1385-1390).

These data point out the role of HER3 in the development of cancer and demonstrate the great potential of HER3 specific target therapies for the therapy of cancer and other malignancies characterized by hypersignaling through HER3 and/or its heterodimerization partners induced signaling pathways (Reviewed in Citri and Yarden, Nat Reviews Mol Cell Biol, 2006 (7), 505-516; Shawver et al, Cancer Cell, 2002 (1), 117-123; Yarden and Sliwkowski, Nat Reviews Mol Cell Biol, 2001 (2), 127-137).

Agents and methods capable of treating HER3 associated diseases have been described before. For example anti-HER3 antibodies described in WO 03/013602 are reported to induce accelerated receptor internalization and to reduce tumor cell proliferation and migration. In U.S. Pat. No. 5,968,511 (corresponding to WO 97/135885) HER3 antibodies were found to reduce ligand-induced formation of HER2/HER3 heterodimers. WO 00/078347 discloses methods for arresting or inhibiting cell growth, comprising preventing or reducing HER2/HER3 heterodimer formation, for example, by administering a combination of an anti-HER2 antibody, e.g. Herceptin, and an anti-HER3 antibody, e.g., antibody 105.5 purchased from Neomarkers.

Based on the increasing implication of uncontrolled signal transduction in many pathological conditions including cancer, a principle aim of medical/pharmaceutical drug development is the development of individual or targeted therapies for the treatment of diseases. Such specific therapies may e.g. comprise therapeutic antibodies, small molecule inhibitors, nucleic acid interference, and the administration of an individually selected or dosed pharmaceutical composition.

Most of these so called target specific therapies predominantly affect a single target. Thus it is critical in modern drug development to identify those patients responsive to the target specific therapy.

A very prominent example is the therapeutic antibody Herceptin that is directed against the receptor tyrosine kinase HER2. This particular antibody has been approved for the treatment of breast cancer, a tumor indication which is associated with an amplification of the HER2 gene in about 20% of cases causing overexpression of the corresponding protein. In order to differentiate those 20% of patients which would benefit from the antibody therapy from the 80% that would not, a diagnostic assay, HercepTest, has been developed.

However, such assays including HercepTest only detect the amount of the targeted protein, whereas often it is the activity of the protein that is actually causing the cellular signal deregulation and subsequent malignancy. For example, the HercepTest only predicts a successful patient response in approximately 30% of the cases when Herceptin is used as a single agent (Leyland-Jones, Lancet Oncol (2002) March; 3(3):137-44). This low predictive rate is observed even though all of the patients treated are judged to be overexpressing HER2, demonstrating the significant limitations of this type of diagnostic assay and the need for identifying better biomarkers of responsiveness to therapy.

Another critical step during drug development is the selection of the dose for therapeutic agents. Usually, in case of non-targeted conventional drugs the assumption of the maximally tolerated dose is used. This same principle, however, does not apply for targeted therapies, where an optimal biologic dose would be preferred instead. In fact the definition of the optimal dose to be administered may be defined by pharmacodynamic or -kinetic parameters and the determination of the efficacy on the target molecule (Albanell et al., 2002, J. Clin. Oncol. 20, 110-124). Therefore, it is desirable to have a robust test system to determine pharmacodynamic parameters, such as for example sufficient solubility and stability of a compound that allows delivery to the site of action in sufficient concentration, metabolic stability so that the compound is not cleared from the body so rapidly that it does not have a chance to be an effective pharmacological agent, or pharmacokinetics that allow the compound to reach a desired plasma/serum concentration.

Successful development, approval and use of targeted drugs will often depend in large part upon the ability of the developer or clinician to determine before and during treatment the activation status of the specific protein which the drug is targeted against. Another aspect of pharmacodynamic correlation is the dose response for a given therapeutic and the desirable (treatment) and undesirable (adverse events) effects. Careful assessment of the risk-benefit-ratio of a given new drug (-combination) will lead to a tolerable administration and a successful completion of the therapeutic intervention. The assessment of potential resistance markers after completion of treatment is the final aspect of pharmacodynamic effects that would influence the decision on further treatment.

However, in clinical routine it is difficult to assess the biological and pharmacodynamic effects of therapeutic agents. In general, pharmacodynamic effects can be measured through extensive imaging and radioactive labeling of substance or substrate (e.g. PET, CT) and the read-out is to be compared with the observed side effects and clinical efficacy. For many therapeutics (including targeted therapeutics) so-called surrogate markers for biological efficacy (PD markers) have been defined and are followed during the course of therapy. However, these markers don't indicate the direct biological effect of the therapeutic on normal and/or cancerous cells and therefore may be subject to off-target effects and activation/deactivation through external (not target specific) pathways. Examples for these markers are CA-125, KI67, PTEN, and βHCG. A desirable marker would be specific to the pathway and the therapeutic (targeted) intervention, easily accessible and analyzable without intra- and/or intersubject variability.

In a specific case, the functional role and expression of epidermal growth factor, EGF, and its cognate receptor, EGFR, in the skin were correlated with the pharmacological side effects of anti-EGFR therapy such as skin rash and hair loss (Lacouture at al. (2006), Nat. Rev. Cancer 6, 803-812). In particular, by using a sample derived from adult skin keratinocytes as surrogate marker tissue, treatment of tumor patients with for example the EGFR inhibitor, ZD1839, can be monitored by analyzing the inhibition of EGFR tyrosine phosphorylation through immunohistochemical methods (Albanell et al., 2002), supra).

Nevertheless, presently applied methods for determination of pharmacodynamic and -kinetic parameters are of limited use. Whereas traditional methods are often too broad for individual therapies, other methods such as the detection of EGFR are target restricted.

Thus, the technical problem underlying the present invention was to provide a rapid, quantitative, reproducible, and inexpensive assay that is compatible with current clinical laboratory instrumentation and which is suitable for determination of the activation and/or expression level of HER receptors.

The solution of the above problems is achieved by providing the embodiments characterized in the claims.

According to the present invention, a method for the determination of the sensitivity or responsiveness of a disease to a HER modulator or to a combination of at least one HER modulator with a further agent is provided. For example, based on the surprising finding that the sensitivity of tumor cell growth to inhibition by a HER3 modulator correlates with HER3 receptor activation, e.g. phosphorylation, methods and procedures have been devised for predicting the responsiveness of a subject to treatment with a HER modulator.

The results presented in the examples herein demonstrate that tumor cells, such as BxPC3 (pancreas cancer), A431 (epithelial carcinoma) or A549 (lung carcinoma) grown in vitro express HER3 and show basal HER3 phosphorylation. Further experiments validated these initial findings in a majority of the examined tumor cell lines. Interestingly, examination of tumor xenograft models treated with HER3 inhibitors showed that those tumors arising from tumor cell lines with HER3 expression and elevated basal HER3 phosphorylation, e.g. T47D (breast cancer), BxPC3 (pancreas cancer), HT-29 (colon cancer) and CaLu-3 (NSCLC) are particularly responsive to treatment protocols targeting a HER3 receptor. The data indicate that HER receptor activation, e.g. phosphorylation, may be a general biological switch that predefines the level of responsiveness of a disease to HER modulators. Thus, activation of a HER receptor such as HER3 is indicative of a disorder that is particularly sensitive to treatment with a HER modulator.

Accordingly, a first aspect of the invention relates to a method for determining whether a disease is responsive to treatment with a HER modulator, by obtaining at least one sample from a subject at risk of or having said disease, examining the expression and/or activity of at least one HER receptor in a cellular assay, and identifying a disease as responsive if expression and/or activity of at least one HER receptor is detected.

The term "HER receptor" is intended to mean a HER1 protein, e.g. human HER1/EGFR (Acc-Nr. Swiss Prot P00533), a HER2 protein, e.g. human HER2 (Acc-Nr. Swiss Prot P04626), a HER3 protein, e.g. human HER3 (Acc-Nr. Swiss Prot P21860) or a HER4 protein (Acc-Nr. Swiss Prot Q155503). Preferably, the HER receptor is a HER3 protein, more preferably the human HER3 protein.

In another preferred aspect the present invention relates to the use of a modulator that affects a HER receptor selected from the group of HER1, HER2, HER3 or HER4. In particular, a modulator that affects the activity of HER3, e.g. human HER3, is preferred.

The term "HER modulator" is intended to mean a compound or drug that acts either on the nucleic acid level or on the protein level to directly or indirectly modulate HER receptor activity. Direct or indirect modulation includes activation or inhibition of HER receptor activity or HER receptor signal transduction pathway. Preferably, the modulation includes an inhibition.

The modulator of HER receptor activity may act on the nucleic acid level, either on the transcription or on the gene itself. On the gene level said modulator may cause a partial or complete gene inactivation, for example by gene disruption. Reducing or inhibiting transcription may comprise application of effector nucleic acids, such as antisense molecules, for example DNA or RNA molecules or RNA analogues, ribozymes, small double-stranded RNA molecules capable of RNA interference (siRNA) or microRNAs. Further, precursor RNA molecules of siRNA or DNA molecules encoding the latter may be suitable.

Effector molecules may be directly introduced into a cell or generated within a cell by transcription from suitable nucleic acid templates. Production and uses of effector nucleic acids are extensively discussed in the literature and are widely known and available to one skilled in the art.

In another embodiment, the HER modulator may act on the protein level by at least partially inhibiting HER receptor mediated signal transduction. For example the modulator may block the ligand induced activation of a HER receptor. By a ligand is meant a polypeptide that binds to and/or activates a HER receptor. Preferred examples of ligands are selected from the group of:

| | |
|---|---|
| AMPR (amphiregulin) | NM 001657 |
| BTC (betacellulin) | NM 001729 |
| DTR (diphtheria toxin receptor (heparin-binding epidermal growth factor-like growth factor)) | NM 001945 |
| EGF (epidermal GF, beta-urogastrone) | NM 001963 |
| EREG (epiregulin) | NM 001432.1 |
| NRG1 (neuregulin 1) | NM 013957 |

-continued

| | |
|---|---|
| NRG2 (neuregulin 2) | NM 013982 |
| NRG3 (nauregulin 3) | AL096076 |
| NRG4 (neuregulin 4) | NM 138573 |
| TGFA (transforming growth factor, alpha) | NM 003236 |

Particularly preferred are neuregulin 1 isoforms encoded by the neuregulin 1 gene.

Accordingly, such a modulator may act by occupying the ligand binding site or a portion thereof of the HER receptor, thereby making the receptor inaccessible to its natural ligand so that its normal biological activity is prevented or reduced. In this embodiment, ligand muteins capable of binding to the receptor, but unable to induce signal transduction, or antibodies directed against ligands are examples of HER modulators. Suitable types of antibodies are discussed in detail below.

In another aspect the modulator interferes with ligand dependent or independent formation of HER receptor oligomers, e.g. hetero-oligomers or homo-oligomers. An HER receptor hetero-oligomer herein is a non-covalently associated oligomer comprising at least two different HER receptors. A HER receptor homo-oligomer is a non-covalently associated oligomer that comprises at least two HER receptors of the same. Examples of such HER oligomers include, but are not limited to HER1/HER1, HER1/HER2, HER1/HER3, HER1/HER4, HER2/HER2, HER2/HER3, HER2/HER4, HER3/HER4, HER4/HER4. Moreover, preferred hetero-oligomers may comprise one, two or more HER2 receptors combined with a different HER receptor, such as HER1, HER3, or HER4. Other proteins, such as a cytokine receptor subunit (e.g., gp130) or other receptor tyrosine kinases such as the IGF-1R may also be included in the hetero-oligomer.

A reduction of HER receptor mediated signal transduction may be further caused by a downregulation from the membrane and/or degradation of HER receptor resulting in an at least partial disappearance of HER molecules from the cell surface or by a stabilization of HER molecules on the cell surface in a substantially inactive form, i.e., a form which exhibits a lower signal transduction compared to the non-stabilized form.

Alternatively, a reduction of HER mediated signal transduction may also be caused by influencing, e.g. decreasing or inhibiting, the binding of a signal transduction molecule, e.g. PI3K, Shc or Grb7 to HER-3, of GRB2 to HER-2, of GRB2 to SHC, or by inhibiting AKT phosphorylation, PYK2 tyrosine phosphorylation or ERK2 phosphorylation. Negative regulators, such as PTPs or proteases, could also be influenced.

In another aspect the HER modulator may be an antibody or a fragment thereof, directed against a HER receptor. The antibody may be a monoclonal or polyclonal antibody, as well as a recombinant antibody, e.g. single chain antibody or a fragment thereof, which contains at least one antigen-binding site, an antibody fragment such as a Fab, Fab' or F(ab')$_2$ fragment or a recombinant fragment such as a scFv fragment and a humanized antibody or a human antibody. For therapeutic purposes, particularly for the treatment of a candidate in need thereof, the application of chimeric antibodies, humanized antibodies or human antibodies is especially preferred.

In a preferred embodiment of the present invention an anti-HER3 antibody is selected from the group consisting of antibody 105.5 (Chen et al, JBC 1996, 271 (3) 7620-9), SGP-1 (Rajkumar et al, The Breast 1995, 4 84-91), H3 90.6 (Chen et al, JBC 1996, 271 (3) 7620-9), 1B4C3 and 2D1D12 (PCT/EP02/08938) or one of the human anti-HER3 antibodies disclosed in U.S. 60/755,022. An anti-HER2 antibody is selected from the group consisting of Trastuzumab, Pertuzumab, Herceptin-geldanamycin, 213-bi-Herceptin-alpha conjugate, Herceptin-DM1 and an anti-HER1 antibody is selected from the group consisting of Panitumumab, Cetuximab, Matuzumab, Erbitux-paclitaxel conjugate, Erbitux-MMC (mitomycinC) and LA22-MMC.

Another example of a modulator in terms of the methods of the present invention is a scaffold protein, having an antibody like binding activity that binds to a HER family member. Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun, (2005) Curr Opin Biotechnol, 16, 459-69). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against a HER family member, either purified protein or protein displayed on the cell surface, for binding agents in an artificial scaffold library displayed in vitro, skills which are known in the art (Binz and Plückthun, 2005, supra). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. Insertion can be accomplished by various methods known to those skilled in the art including, for example, polypeptide synthesis, nucleic acid synthesis of an encoding amino acid as well by various forms of recombinant methods well known to those skilled in the art.

Reducing or inhibiting of HER activity on the protein level may be also achieved by application of low molecular weight inhibitors. Examples of low molecular weight inhibitors may include organic compounds, organometallic compounds, salts of organic and organometallic compounds, saccharides, amino acids, and nucleotides. Low molecular weight inhibitors further include molecules that would otherwise be considered biological molecules, except their molecular weight is preferably not greater than 600, more preferably not greater than 450. Thus, low molecular weight inhibitors may also be lipids, oligosaccharides, oligopeptides, and oligonucleotides and their derivatives. These molecules are merely called low molecular weight inhibitors because they typically have molecular weights not greater than 600 and the term shall not be construed as restricted to a specific molecular weight. Low molecular weight inhibitors include compounds that are found in nature as well as synthetic compounds.

In one embodiment, the HER modulator is a low molecular weight inhibitor that inhibits cell growth. In another embodiment, the HER modulator is a low molecular weight inhibitor that inhibits at least partially HER mediated signal transduction. A variety of low molecular weight inhibitors directed against HER receptors have been described. For example in one embodiment of the present invention the low molecular weight inhibitor is one of the group comprising Gefitinib, Erlotinib, Lapatinib, BIBW2992, AV412. In another embodiment the low molecular weight inhibitor belongs to the group of indirect HER modulators such as kahahalide F (Janmaat et al, 2005) or estrogen receptor inhibitors such as tamoxifen.

The invention also encompasses combinations of HER modulators, e.g. HER modulators directed against the same receptor, e.g. HER3, or HER modulators directed against different HER receptors, e.g. HER3 and HER1, HER3 and HER2, and HER3 and HER4. For example, combinations of antibodies may be used.

The present invention further relates to a method for determining responsiveness of disorder to the administration of at least one modulator of a HER receptor and/or a further agent as described in detail below.

The active ingredient, e.g. the HER modulator is usually administered as a pharmaceutical composition. The composition may be in solid, liquid or gaseous form and may be, inter alia, in a form of (a) powder(s), (a) tablet(s), (a) solution(s) or (an) aerosol(s). Said composition may comprise at least one, e.g. two, three, four, or five active compounds.

The pharmaceutical composition is useful for the treatment of a disease as referred to below. In a preferred embodiment, said disease is a hyperproliferative disease, an inflammatory disease or a neurodegenerative disease. The hyperproliferative disease may comprise, but is not limited to psoriasis or breast, lung, colon, kidney, lymphoma, skin, ovary, prostate, pancreas, esophagus, barret, stomach, bladder, cervix, liver, thyroid cancer, soft tissue sarcoma, melanoma or other hyperplastic or neoplastic diseases associated with HER receptor expression, overexpression and/or activation.

As indicated above, the pharmaceutical composition may comprise at least one further active agent. Examples for additional active agents, which may be used in accordance with the present invention, are antibodies or low molecular weight inhibitors of other receptor protein kinases, such as IGF-1R, or c-met, receptor ligands such as vascular endothelial factor (VEGF), cytotoxic or anti-neoplastic agents, such as doxorubicin, platinum compounds such as cis-platin or carboplatin, cytokines, antisense molecules, aptamers, or siRNA molecules. Many antineoplastic agents are presently known in the art. The cytotoxic or antineoplastic agent may be selected from the group of therapeutic proteins including, but not limited to, antibodies or immunomodulatory proteins, or from the group of small molecule inhibitors or chemotherapeutic agents consisting of mitotic inhibitors, kinase inhibitors, alkylating agents, anti-metabolites, intercalating antibiotics, growth factor inhibitors, cell cycle inhibitors, enzymes, topoisomerase inhibitors, histone deacetylase inhibitors, anti-survival agents, biological response modifiers, anti-hormones, e.g. anti-androgens, and anti-angiogenesis agents. When the anti-neoplastic agent is radiation, treatment can be achieved either with an internal (brachytherapy BT) or external (external beam radiation therapy: EBRT) source.

The term "disease" when used in the present invention shall mean any condition that would benefit from a medical treatment or that is associated with an abnormal HER receptor expression, activation and/or signal transduction. This includes chronic and acute diseases or diseases including those pathological conditions which predispose the candidate to the disease in question. A preferred disease to be treated in accordance with the present invention is a hyperproliferative disease. A hyperproliferative disease as mentioned above includes any neoplasia, i.e. any abnormal and/or uncontrolled new growth of tissue. The term "uncontrolled new growth of tissue" as used herein may depend upon a dysfunction and/or loss of growth regulation. A hyperproliferative disease further includes tumor diseases and/or cancer, such as metastatic or invasive cancers. In a particular preferred embodiment of the method of the present invention, said hyperproliferative disease is in brain, central nervous system, soft-tissue sarcoma, hematological malignancies, oral cavity, head and neck, breast, lung, colon, gastric, kidney, lymphoma, skin, ovary, prostate, pancreas, esophagus, bladder, cervix, liver, thyroid cancer, melanoma, cancer of unknown origin, or other hyperplastic or neoplastic diseases associated with HER receptor expression, overexpression and/or activation, e.g. hyperphosphorylation.

A disease which is associated with the expression or overexpression of a HER receptor, is a disease with cells comprising on their cell surface a HER receptor protein and/or a ligand binding to a HER receptor. For example a disease which "expresses" a HER family member is one which has significantly higher levels of an HER receptor, such as HER3, at the cell surface thereof, compared to a healthy cell of the same tissue type. Such expression may be caused by gene amplification or by increased transcription or translation. HER receptor expression may be determined in a diagnostic or prognostic assay by evaluating levels of the HER protein present on the surface of a cell (e.g., via immunohistochemistry; IHC). Alternatively, or additionally, one may measure levels of HER-encoding nucleic acid in the cell, e.g., via fluorescent in situ hybridization (FISH; see WO 98/45479 published October, 1998), Southern blotting, or polymerase chain reaction (PCR) techniques, such as real time quantitative PCR (RT-PCR). Expression of the HER ligand, may be determined diagnostically by evaluating levels of the ligand (or nucleic acid encoding it) in the patient by various diagnostic assays such as DNA arrays, Northern blotting, FISH, Southern blotting, PCR or protein based assays described above. In addition the presence of various N-terminal HER3 isoforms or serum concentrations of shed receptor domains may be evaluated when practicing the present invention.

Aside from the above assays, various other assays are available to the skilled practitioner. For example, one may expose cells within the body of the patient to an antibody which is optionally labelled with a detectable label, e.g., a radioactive isotope, and binding of the antibody to cells in the patient can be evaluated, e.g., by external scanning for radioactivity or by analyzing a biopsy taken from a patient previously exposed to the antibody.

In a further aspect of the invention, the disease may be associated with HER activation. Activation of a HER family member may generally involve formation of HER oligomers, followed by activation of the intrinsic receptor kinase activity, the binding of intracellular second messenger molecules to the receptor and/or modification, e.g. tyrosine phosphorylation, of the HER receptor and/or the second messenger molecules, which leads to specific biologic responses, as for example cell proliferation, cell migration or anti-apoptosis.

Another aspect of the present invention is concerned with a method for determining and/or predicting the sensitivity of a disease or condition associated with HER receptor mediated signal transduction to a HER modulator, optionally in combination with a further agent, comprising analyzing a sample by detecting the expression and/or activity of a HER receptor in that sample. Preferably, the method comprises detecting the expression and/or activity of a HER3 receptor. More preferably, the method comprises detecting the activity, e.g. the degree of the phosphorylation of a HER3 receptor.

For example, according to the present invention, the method may be used for the detection of a HER receptor in a cell, for the determination of HER receptor concentration in subjects suffering from a disease as mentioned above or for the staging of said disease in a subject. In order to stage the progression of a disease in a subject under study, or to characterize the response of the subject to a course of therapy, the amount of the HER receptor present in the sample and/or its activation level is determined in a tissue sample, taken from the subject. The amount so identified correlates with a stage of progression or a stage of therapy identified in the various populations of diagnosed subjects, thereby providing a determination of the disease stage in the subject under study. The amount and/or activity of the HER receptor present in the disease tissue may be assessed by immunohistochemistry, ELISA or antibody arrays including phospho-specific antibodies using HER receptor and/or other signal transduction antibodies. Other suitable methods may include bead-based technologies such as Luminex bead assays and proteomics approaches (2-D gels, MS analysis etc). Cellular preparations with methodical prerequisites such as phosphatase inhibitors (ortho-Vanadate, Suramine, $H_2O_2$ or specific inhibitors) as would be the case with phosphatase inhibitor tablets, could be envisioned as part of the quantification of phospho-specific antigen/epitopes.

Other parameters of diagnostic interest and which may form part of the present invention are the oligomerization state as well as the oligomerization partners of a HER receptor. Protein analytical methods to determine those parameters are well known in the art and are among others western blot and immunoprecipitation techniques, FACS analysis, chemical crosslinking, bioluminescence resonance energy transfer (BRET), fluorescence resonance energy transfer (FRET) and the like (e.g. Price et al, Methods in Molecular Biology, 218: 255-268 (2002) or the eTag technology (WO 05/03707, WO 04/091384, WO 04/011900).

The kinase activity can be measured by capturing the kinase in the cell lysate by an antibody with immunoprecipitated and is then subjected to kinase activity reactions in the presence of $^{32}P$-γ-TP. The activity of the kinase in the reaction is analyzed by sodium dodecyl sulfate (SDS)-polyacrylamide gel electrophoresis (PAGE) and autoradiography. Alternatively, in vitro kinase assays can be performed with non-radioactive detection methods (e.g. CST kinase assays) or synthetic peptides that can serve as substrates for a HER receptor, such as HER3, can be spotted on arrays for estimating HER kinase activity.

In another aspect of the present invention the activation level of a HER receptor correlates with the activation status of a second messenger molecule involved in HER receptor mediated signal transduction. Thus one embodiment of the present invention refers to a method for identifying the responsiveness of a disease to treatment with a HER modulator, by obtaining at least one sample from a subject at risk of or having said disease, examining the expression and/or activity of at least one molecule involved in HER receptor mediated signal transduction in a cellular assay, and identifying a disease as responsive if expression and/or activity of at least one a molecule involved in HER receptor mediated signal transduction is detected. Preferably, the expression and/or activity of HER3, optionally in combination with other HER receptors, is examined.

"Signaling pathway" or "signal transduction" refers to a series of molecular events usually beginning with the interaction of a cell surface receptor with an extracellular ligand or with the binding of an intracellular molecule to a phosphorylated site of a cell surface receptor, e.g. a HER receptor, that triggers a series of molecular interactions, wherein the series of molecular interactions results in a regulation of gene expression in the nucleus of a cell. The terms "intracellular molecule", "second messenger molecule", "molecule involved in HER receptor mediated signaling" or "substrate of HER receptor" are used interchangeably herein and refer to molecules involved in HER-mediated signaling pathways as for example reviewed in Citri and Yarden, Nat Reviews Mol Cell Biol, 2006 (7), 505-516; Shawver et al, Cancer Cell, 2002 (1), 117-123; Yarden and Sliwkowski, Nat Reviews Mol Cell Bid, 2001 (2), 127-137. Exemplary molecules that may be part of a HER receptor mediated signaling pathway include, but are not limited to, PI3K proteins, AKT proteins, Grb2 proteins, Grb7 proteins, Shc proteins, Gab-1 proteins, Sos proteins, Src proteins, Cbl proteins, PLCγ proteins, Shp2 proteins, GAP proteins, Vav proteins, Nck proteins and Crk proteins.

In a preferred embodiment of the present invention the phosphorylation state of one of the HER receptors or their substrates can be assessed as a measure of expression and activation of the receptor. As is well known in the art, phosphorylation of a HER receptor indicates that the receptor has been activated and is the mechanism for transducing the downstream signal.

Phosphorylation of one or multiple tyrosine residues in a HER receptor or in one or more of its substrates can be analysed using various tyrosine phosphorylation assays. For example HER receptors or their substrates may be immunoprecipitated with specific antibodies from lysates of cells expressing HER receptors and their substrates and then assayed for tyrosine phosphorylation activity using a phosphotyrosine monoclonal antibody (which is optionally conjugated with a detectable label). In a preferred embodiment tyrosine phosphorylation of HER receptors and their substrates is detected by using phospho-specific antibodies. In a particular embodiment said phospho-specific antibody is selected from the group comprising phospho-specific HER3 antibodies 21D3 (Y1289, Cell Signalling Technology, USA) and 50C2 (Y1222, Cell Signalling Technology, USA), as well as pEGFR, pHER2, pHER4, pIGF-1R, pAkt, pErk, pBad, pp70-S6K, pGSK, p-src, pPyk2, with all relevant phosphotyrosines in a given protein being covered here.

In general, the term "phospho-specific antibody" is meant to represent either a polyclonal or a monoclonal antibody that binds to a phosphorylated epitope in a HER receptor and/or a second messenger molecule associated with HER mediated signal transduction. For example the phosphorylated epitope may include at least one phosphorylated serin-residue. In a preferred aspect of the present invention the phosphorylated epitope may include at least one phosphorylated tyrosine residue. In a particular preferred embodiment of the present invention the phospho-tyrosine residue is selected from the group consisting of Y1054, Y1197, Y1199, Y1222, Y1224, Y1260, Y1262, Y1276, Y1289 and Y1328 in the HER3 protein (numbering according to Kraus et al, PNAS 1989 (86) 9193-9197). The term also encompasses a phospho-specific recombinant antibody, e.g. single chain antibody or a fragment thereof, which contains at least one antigen-binding site, an antibody fragment such as a Fab, Fab' or $F(ab')_2$ fragment or a recombinant fragment such as a scFv fragment and a humanized antibody or a human antibody directed against a phosphorylated epitope in a HER receptor and/or a molecule associated with HER mediated signal transduction.

Phospho-specific polyclonal antibodies can be obtained by methods well known in the art. For example any animal, which is known to produce antibodies can be immunized with a phospho-HER receptor polypeptide. Antibody containing sera is isolated from the immunized animal and is screened for the presence of antibodies with the desired specificity using methods as for example, ELISA or FACS.

Methods for the production of monoclonal antibodies produced by the hybridoma method are first described by Köhler et al., Nature, 256:495 (1975). Monoclonal antibodies can also be produced by recombinant DNA methods (see, for example, U.S. Pat. No. 4,816,567) or may be isolated from phage antibody libraries using the techniques described in Clackson et al., Nature, 352:624-628 (1991) and Marks et al., J. Mol. Biol., 222:581-597 (1% I), for example.

Humanized forms of the antibodies may be generated according to the methods known in the art such as chimerization or CDR grafting. The present invention also relates to a hybridoma or recombinant cell line, which produces the above described monoclonal antibodies or binding fragments thereof.

A disease which is responsive to treatment shows statistically significant improvement in response to a HER modulator treatment when compared to no treatment or treatment with placebo in a recognized animal model or a human clinical trial. The terms "treat" or treatment" refer to both therapeutic treatment and prophylactic or preventative measures, wherein the object is to prevent or slow down (lessen) an undesired physiological change or disorder, such as the development of a hyperproliferative disease, e.g. cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The present invention provides a method of treating a subject in need thereof, comprising determining expression and/or activation of a HER receptor in said subject, and administering to a subject in which HER receptor expression and/or activation has been determined, a therapeutically effective amount of a HER modulator and optionally at least one further agent. Preferably, activation of the HER receptor is determined. More preferably, the HER receptor is HER3.

Depending on the type of the HER modulator, type and severity of the condition to be treated, about 0.01-10000 mg of the HER modulator may be administered to a patient in need thereof, e.g. by one or more separate administrations or by continuous infusion. A typical daily dosage might range from about 0.001 mg/kg to about 1000 mg/kg or more, depending on the factors mentioned above. For repeated administrations over several days or longer, depending on the condition to be treated, the treatment is sustained until a desired suppression of disease symptoms occurs.

The dose of the at least one antineoplastic agent administered depends on a variety of factors. These are, for example, the nature of the agent, the tumor type or the route of administration. It should be emphasized that the present invention is not limited to any dose.

Furthermore the present invention provides additional methods and procedures to evaluate the therapeutic efficacy of a HER modulator or a pharmaceutical composition comprising a HER modulator and/or at least one further agent.

Determination of the pharmacodynamics of a modulator targeting a HER receptor and/or a HER receptor mediated signaling pathway may involve immunohistochemical staining with phospho-specific antibodies of samples of diseased tissue, e.g. tumor tissue, in order to quantitate the activation level of HER receptors and/or related second messenger molecules.

Surprisingly, it was found that relevant pharmacodynamic parameters, e.g. the activation level of a HER3 receptor, may also be determined in primary, i.e. non-diseased normal tissue samples. This allows to establish a rapid, quantitative, reproducible, and inexpensive assay that is compatible with current clinical laboratory instrumentation, wherein the presence of HER3 particularly in its activated form in primary human tissues may be determined, e.g. by immunohistochemistry.

The results presented in the examples herein below demonstrate that human tumor cells express HER3. Surprisingly, very strong HER3 expression and/or activity was also detected in hair follicles. Whereas the expression of total HER3 was located predominantly in the cytoplasm, phosphorylated, i.e. activated HER3 was almost exclusively associated with cell surface membranes.

This finding supported the idea that the presence of activated, e.g. phosphorylated, HER3 in such tissues could be used for an easy and rapid determination of the efficacy of a HER modulator when administered to a subject. For example at least partially reduction of HER3 receptor activation indicates a therapeutically effective amount of said modulator. Conversely no difference in HER3 receptor activity upon treatment with a HER3 modulator correlates with ineffective therapeutic treatment. Thus these findings can form the basis of a new and efficient method for monitoring HER3 receptor directed therapy. Furthermore, hair follicle biopsies could serve as a pharmacodynamic marker for monitoring HER3 modulator directed treatment.

Accordingly the present invention provides a method for determining the therapeutic efficacy of the treatment of a HER receptor, particularly a HER3 receptor-associated disease with a HER modulator and/or a further active agent comprising exposing a subject to the HER modulator and/or the further active agent, obtaining at least one sample from the subject, detecting the activation level of the HER receptor in said sample wherein a difference in the activation level of HER is observed as a result of the exposure to the HER modulator and/or the further active agent as compared to the absence of the exposure to the HER modulator and/or the further active agent.

The term "sample" as embraced by the present invention preferably means the use of a tissue sample for the detection of an activated form of a HER family member or quantification of HER receptor expression. The HER receptor is preferably HER3. The activation level is preferably the degree of phosphorylation.

The term "tissue sample" is meant to include a collection of cells obtained from a tissue of a subject or patient, preferably containing nucleated cells with protein material. The four main human tissues are (1) epithelium; (2) the connective tissues, including blood vessels, bone and cartilage; (3) muscle tissue; and (4) nerve tissue. The source of the tissue sample may be selected from the group comprising of solid tissues as from a fresh, frozen and/or preserved organ or tissue sample or biopsy or aspirate. The present invention also includes the use of samples derived from blood or any blood constituents, bodily fluids such as cerebral spinal fluid, amniotic fluid, peritoneal fluid, or interstitial fluid and cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like.

For use in the present invention the tissue sample is may be a single part or piece of a tissue sample, e.g., a thin slice of tissue or cells cut or micro-dissected from a tissue sample. Generally, tissue arrays can be formalin-fixed tissue samples cut into thin sections and mounted on silanised glass slides that can be used for expression analysis and cellular localization on a protein, RNA or DNA level. In a preferred embodiment at least 10 samples are mounted on one silanised glass slide. In a more preferred embodiment at least 20 samples are mounted on one silanised glass slide. In a most preferred embodiment 40 or more samples are mounted on one silanised glass slide.

The tissue may be fixed (i.e. preserved) by conventional methods known to one skilled in the art. In order to preserve cellular morphology tissue can be fixed in 4% neutral buffered formalin for 16-20 hours and embedded in paraffin.

In a preferred embodiment of the present invention the tissue sample is a hair follicle sample which can be obtained by using a punch biopsy procedure. Suitable areas to be biopsied are the forearm, upper extremity and torso. The selected sites should have visible hair growing.

The size of the biopsy can vary between 2 and 8 mm, whenever possible a specimen with at least 3.5 mm diameter should be harvested. The skin is cleansed and anesthetized. A small needle is used to administer the anesthetic to limit discomfort. The lines of least skin tension should be identified for the area to be biopsied. For example, on the arm, these lines run perpendicular to the long axis of the extremity. The incision line created by the suturing after the biopsy is performed will be oriented parallel to the lines of least skin tension. Physicians who cannot recall the line orientation for a specific body area should consult the widely published drawings of these lines. The skin is stretched perpendicular to the lines of least skin tension. When the skin relaxes after the biopsy is performed, an elliptical-shaped wound remains that is oriented in the same direction as the lines of least skin tension. On the arm, the skin is stretched along the long axis of the extremity. The punch biopsy instrument is held vertically over the skin and rotated downward using a twirling motion. Once the instrument has penetrated the dermis into the subcutaneous fat, or once the instrument reaches the hub, it is removed. The cylindrical skin specimen is elevated with the anesthesia needle. The use of forceps is discouraged because these instruments may cause crush artifacts. The specimen is then cut free from the subcutaneous tissues. The cut is made below the level of the dermis. The wound is closed, if necessary, with one or two interrupted nylon sutures: 5-0 nylon is used for most non-facial areas, and 6-0 nylon for most facial areas. The skin specimen is immediately transferred into buffer medium and processed further for (protein) analysis.

In a particular preferred embodiment suitable areas for the hair collection are the scalp (posterior neck region), the eyebrows and the eyelashes. The number of individual hairs collected can vary between 2 and 6, whenever possible at least 4 individual hair (follicles) should be harvested. Without further anesthesia, the hairs are pulled from the regions previously described. The hairs are inspected for intactness of the shaft and follicle and the suitable specimen will be individually mounted on slides for further processing and protein analysis.

In order to preserve phospho-epitopes in fixed and paraffin-embedded material, tissue samples have to be processed as quickly as possible; i.e. as soon as the surgeon has removed the biopsy material, it needs to be fixed/frozen and subsequently processed. The fixation solutions to be used may depend on the specific phospho-epitopes that are to be analyzed.

The term "therapeutic efficacy" refers to the amount of a HER modulator and/or further agent effective to at least partially block HER receptor activation. The therapeutically effective amount shows beneficial or clinical results as mentioned before. In a preferred embodiment, the therapeutically effective amount may reduce the number of cancer cells, reduce the tumor size, inhibit at least partially cancer cell infiltration into peripheral organs and tumor metastasis, inhibit at least partially tumor growth and/or relieve at least partially one or more of the symptoms associated with the cancer.

Thus the present invention also provides a method for determining the therapeutic efficacy of a HER modulator and/or a further agent in a subject by using the HER receptor activation level as a surrogate marker.

As used herein the term "subject" is meant to be an individual or a patient, either treated or untreated with a HER modulator or pharmaceutical composition comprising a HER modulator and at least one further agent, for any purpose. The term "subject" may also include animals, preferably mammals such as mouse, rat, rabbit, dog, pig and nonhuman primates, e.g. cynomolgous monkey, chimpanzee that are treated with a HER modulator. The term patient refers to a human in need of a treatment with a HER modulator and/or at least one further agent. Preferably the human is in need of such a treatment to treat a hyperproliferative disease, e.g. any neoplastic disease or cancer.

BRIEF DESCRIPTION OF THE DRAWINGS

FIGS. 1a and 1b show basal phosphorylation of HER3 in tumor cell lines;

Figure 2A:
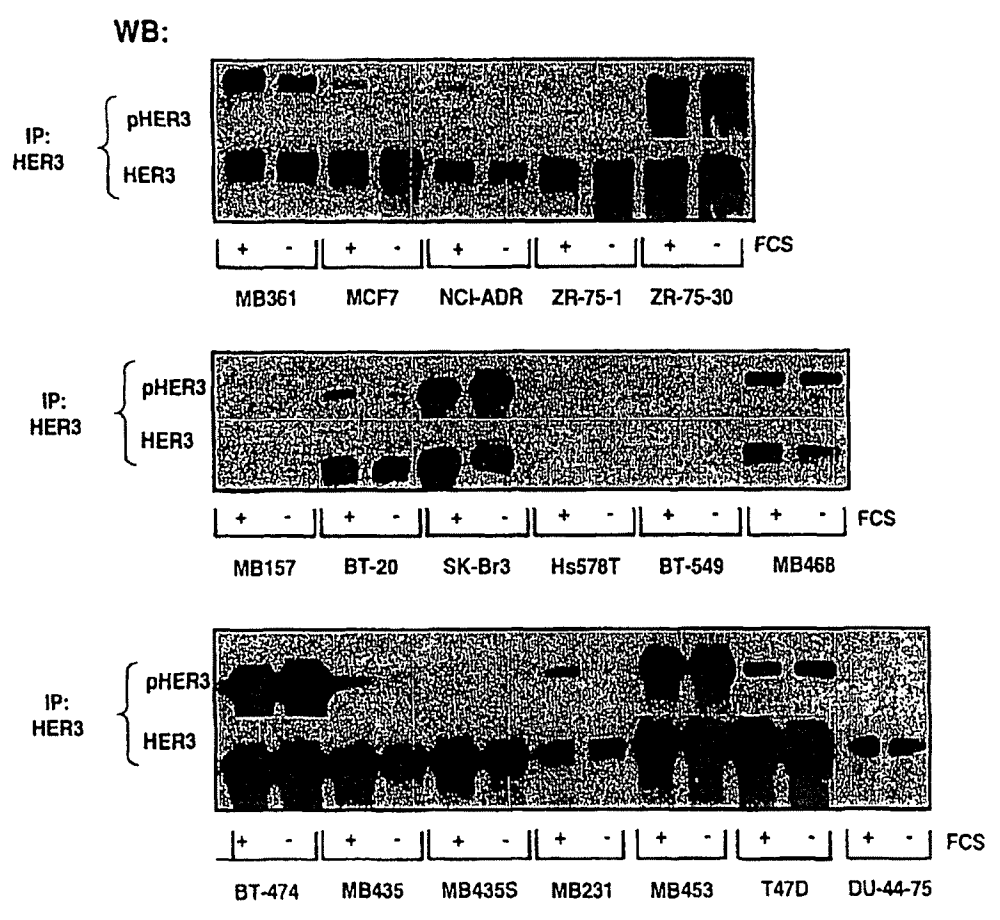

FIG. 2a shows basal phosphorylation and expression of HER3 in breast;

FIG. 2f shows basal phosphorylation and expression of HER3 in melanoma cancer cell lines;

FIG. 3: Correlation between HER3 and pHER3 expression in vitro in all cell lines analysed;

FIG. 4a shows basal phosphorylation and expression of HER3 in selected cancer cell lines;

FIG. 4b: Correlation between pHER3 expression and sensitivity to anti-HER3 treatment;

EXAMPLES

The detection of basal phosphorylation of HER3 was conceived to underlie autocrine receptor activation and represent a selection marker for potentially suitable models in the use of HER3-directed therapeutic intervention. To this end, several cell lines were chosen and analysed for their phospho-HER3 content in the presence or absence of serum. An initial experiment showed that the pancreatic tumor cell line Bx-PC3 contains high levels of basally phosphorylated, i.e. activated HER3 in serum-starved and unstarved cells, indicating that Bx-PC3 may be a suitable model for an anti-HER3 therapeutic approach (FIG. 1a).

Figure 1B:
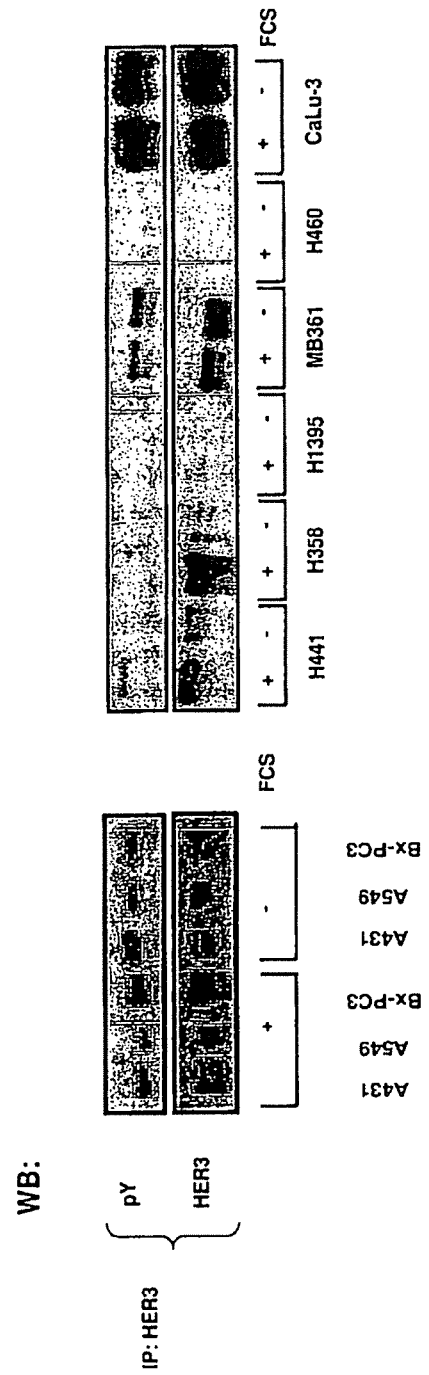
Figure 2B:
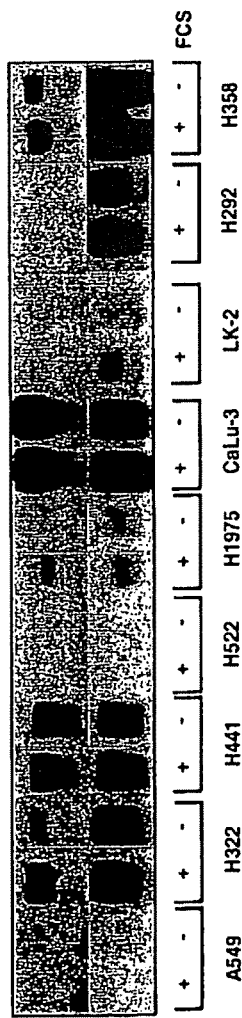
FIG. 2b shows basal phosphorylation and expression of HER3 in lung cancer cell lines.
Figure 2C:
FIG. 2c shows basal phosphorylation and expression of HER3 in colon cancer cell lines.
Figure 2D:
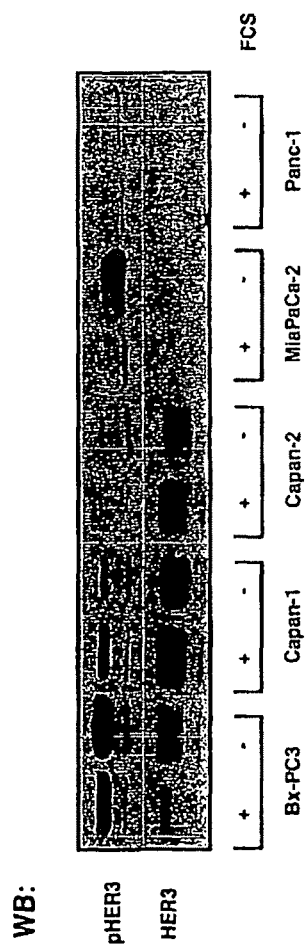
FIG. 2d shows basal phosphorylation and expression of HER3 in pancreas cancer cell lines.
Figure 2E:
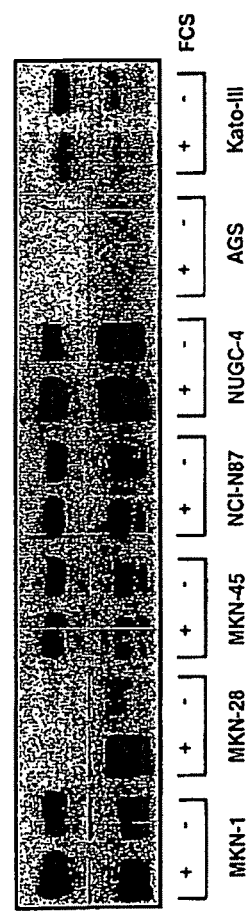
FIG. 2e shows basal phosphorylation and expression of HER3 in gastric cancer cell lines.
Figure 2G:
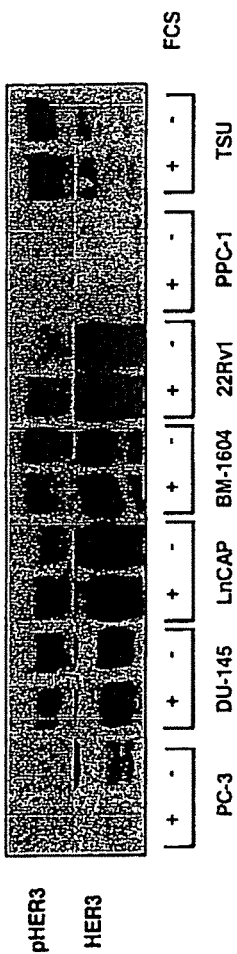
FIG. 2g shows basal phosphorylation and expression of HER3 in prostate cancer cell lines.

Additional experiments confirmed the finding in Bx-PC3 cells and extended the observation of basal HER3 phosphorylation to A549 and A431 cells (FIG. 1b).

Subsequently, based on these findings more cell lines were analyzed systematically and extended to tumor cell lines of 7 different cancer indications (breast, lung, colon, pancreas, prostate, gastric, melanoma) (FIG. 2a-g).

Overall phosphorylated, i.e. activated HER3 was detected in approx. ⅔ of the examined tumor cell lines. No significant difference between serum and serum-starved phosphorylation could be detected (FIG. 3a, b).

The hypothesis that the presence of phosphorylated HER3 in tumor cell lines in vitro implies and predicts responsiveness to HER3-directed intervention was tested in subsequent in vivo studies using cell lines such as Bx-PC3, HT-144, and T47D among others. From these studies, in vivo efficacy was correlated with pHER3 expression in vitro, suggesting that activated HER3 would serve as a surrogate marker for therapy (FIG. 4a, b).

Figure 5A:
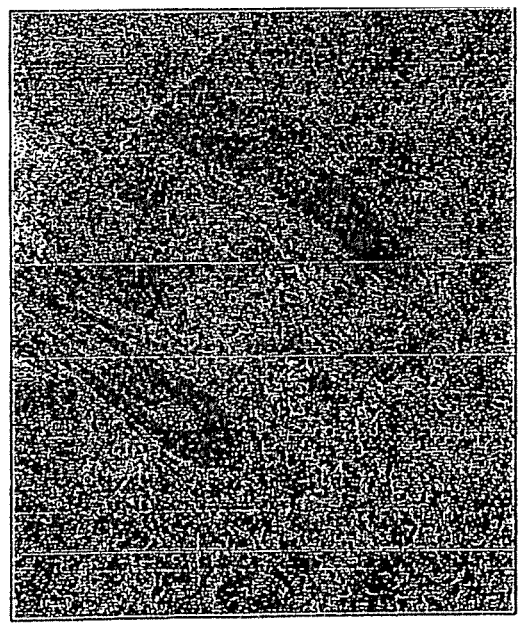
FIG. 5a: HER3 expression in human hair follicles. Immunostaining and peroxidase detection of human hair follicles using monoclonal HER3 antibody.
Figure 5B:
FIG. 5b: HER3 phosphorylation in human hair follicles. Immunostaining and peroxidase detection of pHER3 human hair follicles using monoclonal antibody 21D3 showing high levels of membranous HER3 phosphorylation.

In order to apply the results obtained from in vitro western blot analysis and in vivo animal xenograft experiments to a therapeutically relevant scenario, we investigated the presence of HER3 and its activated form in primary human tissues by immunohistochemistry. Expression of HER3 was detected in a variety of tumor samples, including a prominent presence in melanoma. In contrast, HER3 expression was not detected in normal skin, but—surprisingly—was very strong in hair follicles (FIG. 5a, b).

Figure 6:
FIG. 6: HER3 phosphorylation in human normal tissues. Immunostaining and peroxidase detection of pHER3 human normal tissue using monoclonal antibody 21D3 showing high levels of membranous HER3 phosphorylation. Shown is GI tract (left), testis (middle) and epithelium of the bladder (right).

Whereas the expression of total HER3 was located predominantly in the cytoplasm, phosphorylated, i.e. activated HER3 was almost exclusively associated with cell surface membranes. This finding supported the idea that the presence of phosphorylated HER3 in such tissues could be used for selecting tumor patients responsive to anti-HER3 therapy. Furthermore, as well as monitoring HER3-directed therapy hair follicle biopsies could serve as a pharmacodynamic marker for monitoring HER3-directed treatment. Activated HER3 was also detected in a number of additional normal human tissues, including the GI tract, testis and bladder (FIG. 6).

Figure 7:
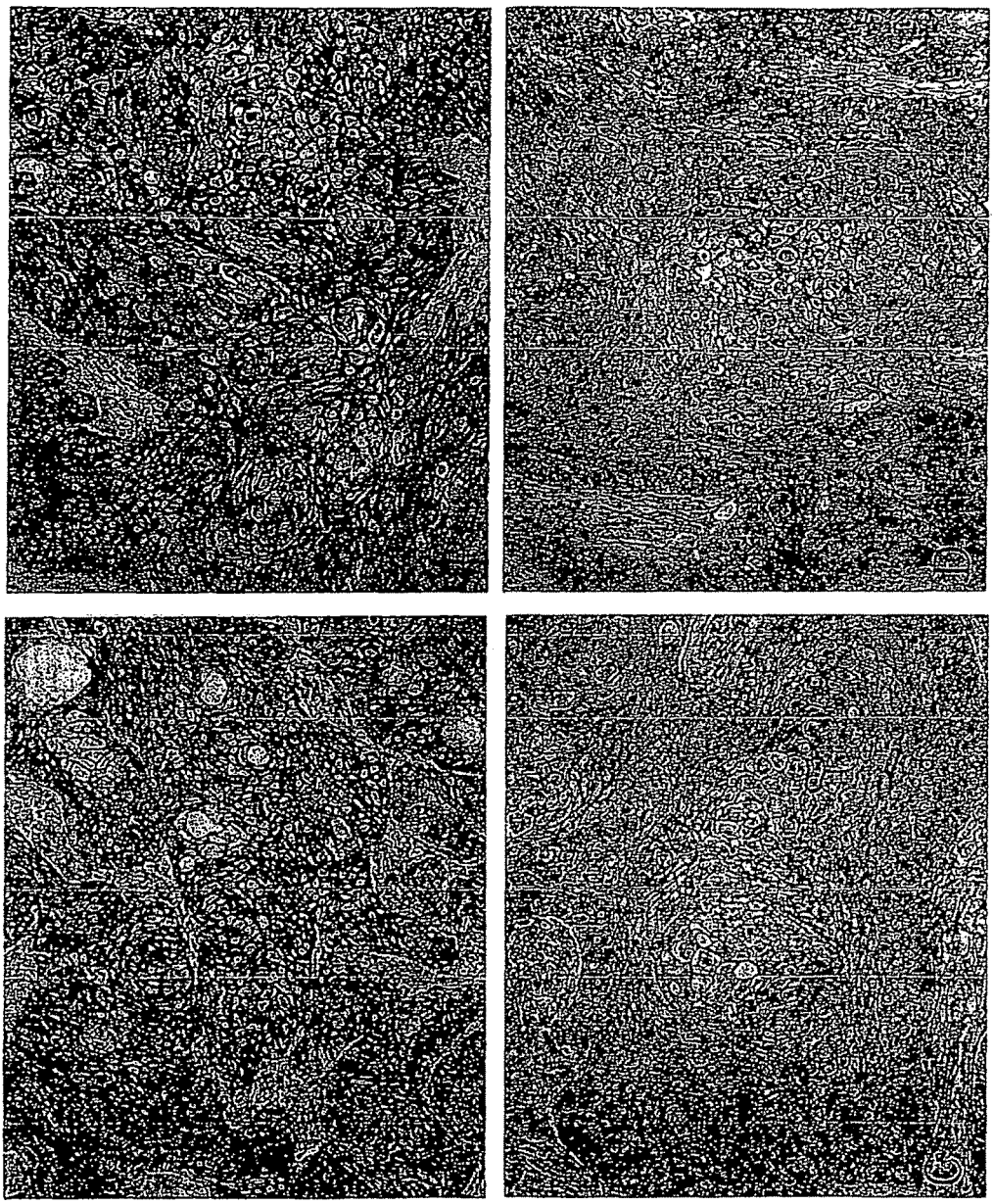
FIG. 7: Immunohistochemical staining with rabbit monoclonal anti-p Her3 antibody (Cell Signalling 21D3, Lot 4 1:650 dilution, 0.074 ug/ml) on FFPE sections of BxPC3 xenografts, 20×.
- (A) and (B) Tumour after administration of control IgG1 500 μg/mouse
- (C) and (D) Tumour after administration of antibody U3-1287 500 μg/mouse
- Stainings were done in duplicate on three independent xenografts.
Figure 8:
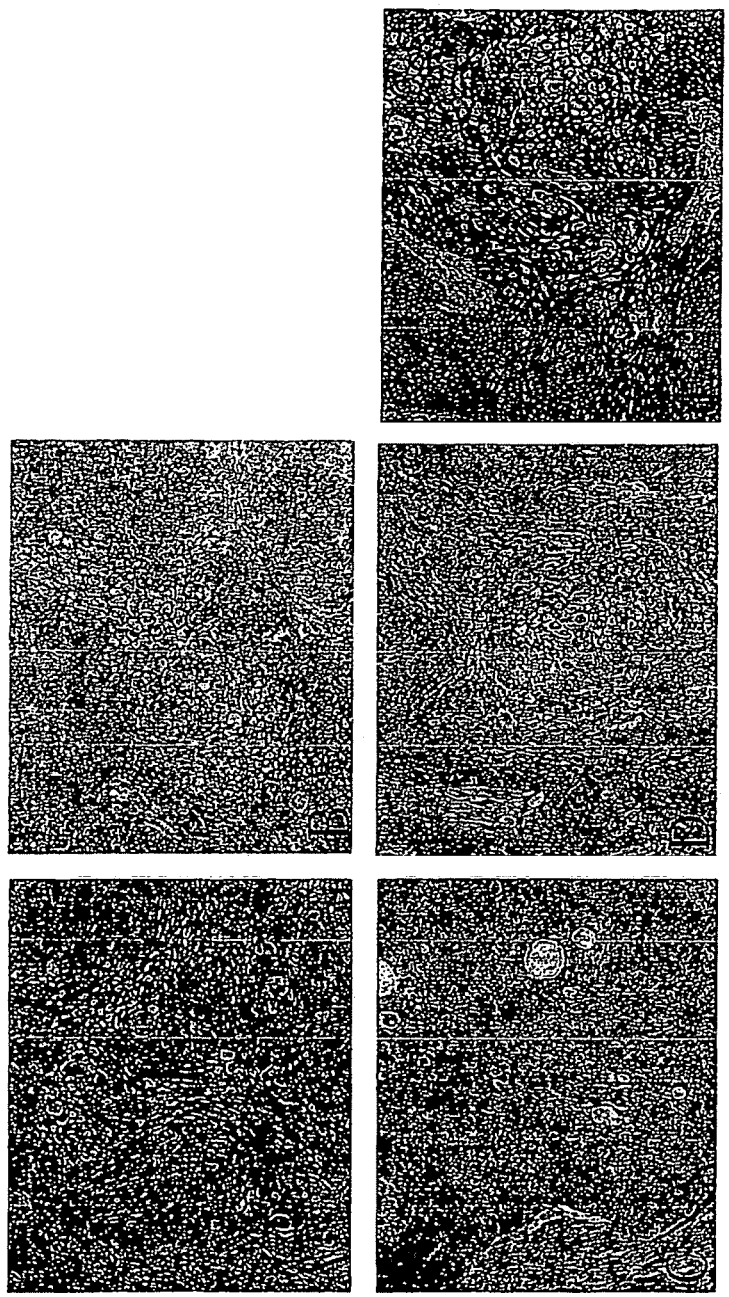
FIG. 8: Immunohistochemical staining with rabbit monoclonal anti-pHer3 antibody (Cell Signalling 21D3, Lot 4 1:650 dilution, 0.074 ug/ml) on FFPE sections of BxPC3 xenografts, 20×.
- (A) Tumour after administration of antibody U3-1287 25 μg/mouse
- (B) Tumour after administration of antibody 03-1287 100 μg/mouse
- (C) Tumour after administration of antibody U3-1287 200 μg/mouse
- (D) Tumour after administration of antibody U3-1287 500 μg/mouse
- (E) Tumour after administration of control IgG1 500 μg/mouse.
- Stainings were done in duplicate on three independent xenografts.
Figure 11:
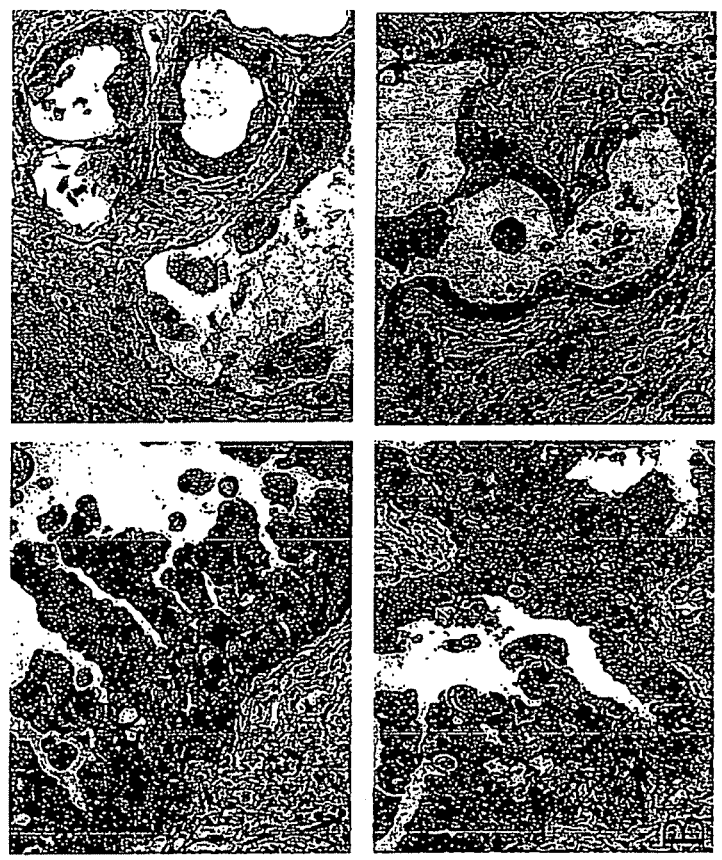
FIG. 11: Immunohistochemical staining with rabbit monoclonal anti pHer3 antibody (Cell Signalling 21D3, Lot 4 1:8000 dilution, 0.006 ug/ml) on FFPE sections Calu-3 xenografts, 40×.
- (A) and (B) Tumour after administration of control IgG1 25 mg/kg 72 h
- (C) and (D) Tumour after administration of antibody U3-1287 25 mg/kg 72 h
- Stainings were done in duplicate on five independent xenografts.

A reduction of membrane staining intensity, a reduction of tumour cells compared to whole cell number in the tumour and a reduction of pHer3 positive cells compared to whole cell number in the tumour was found after administration of anti-HER3 antibody (FIGS. 7, 8 and 11).

Figure 9:
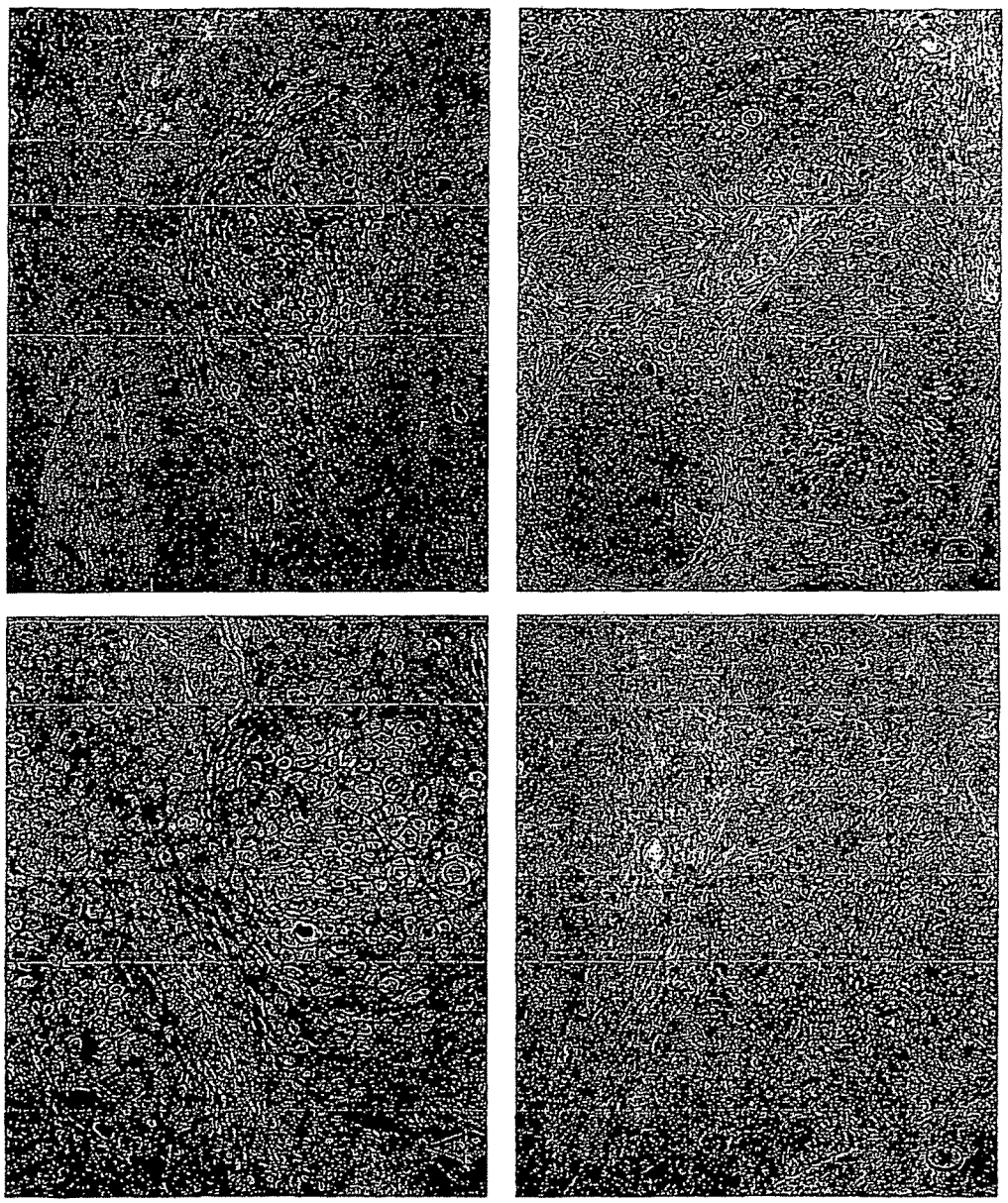
FIG. 9: Immunohistochemical staining with mouse monoclonal anti-Her3 antibody (Dako-H3-IC, 1:250 dilution, 0.52 ug/ml) on FFPE sections of BxPC3 xenografts, 20×.
- (A) and (B) Tumour after administration of control IgG1 500 μg/mouse
- (C) and (D) Tumour after administration of antibody U3-1287 500 μg/mouse
- Stainings were done in duplicate on three independent xenografts.
Figure 10:
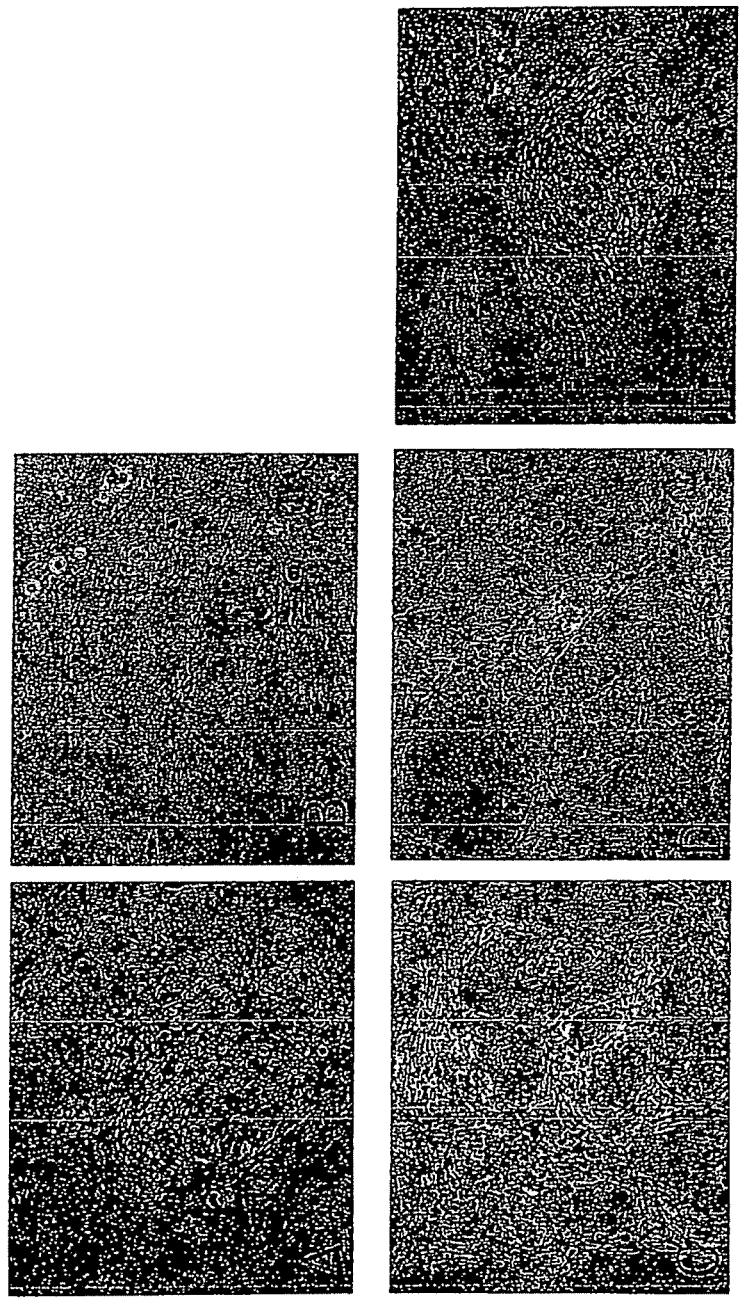
FIG. 10: Immunohistochemical staining with mouse monoclonal anti-Her3 antibody (Dako-H3-IC, 1:250 dilution, 0.52 ug/ml) on FFPE sections of BxPC3 xenografts, 20×.
- (A) Tumour after administration of antibody U3-1287 25 μg/mouse
- (B) Tumour after administration of antibody U3-1287 100 μg/mouse
- (C) Tumour after administration of antibody U3-1287 200 μg/mouse
- (D) Tumour after administration of antibody U3-1287 500 μg/mouse
- (E) Tumour after administration of control IgG1 500 μg/mouse
- Stainings were done in duplicate on three independent xenografts.

Reduction of staining intensity and reduction of Her3 positive cells correlates with reduction in tumour volume (FIGS. 9 and 10).

The role of HER3 in normal skin has not been characterized previously. RNA expression was previously detected in postnatal skin (Kraus et al, 1989) Thus, our present analysis represents the first description in this respect. Surprisingly, we found that HER3 and its activated form are expressed in the hair follicles and in cells of the eccrine and sebaceous glands. This was not expected since the preferred partner of HER3, HER2, has not been reported to be expressed in these tissues This opens up the use of activated HER3 for patients selection etc. In contrast to activated EGFR, activated HER3 is not located intracellularly, but predominantly membranous. Expression of (activated) HER3 was also not observed in normal keratinocytes, where expression of EGFR is widespread (Expression of HER3 is rather low in keratinocytes (Laux et al, 2006). Thus, use of HER3 for diagnosis/selection and therapy may not only provide a regimen with less severe side effects compared to EGFR therapy which causes prominent skin rash, but may prove to be very useful for the monitoring of combination therapy.

HER3 Phosphorylation in Tumor Cell Lines

Cells were seeded in 6-well dishes overnight, serum-starved or cultivated with 10% FCS-containing growth medium for 24 hours and treated with lysis buffer for 20 minutes. Lysate was cleared by centrifugation for 30 min and HER3 was immunoprecipitated from crude lysate with a specific anti-HER3 monoclonal antibody (1B4C3). Immunoprecipitates were incubated for 4 hours at 4° C., washed three times with 1×HNTG (50 mM Hepes pH 7.5, 150 mM NaCl, 10% Glycerine, 1 mM EDTA pH 8.0, 0.1% Triton X-100) and denatured with 3× Laemmli buffer containing b-mercaptoethanol for 5 min at 100° C. The protein samples were separated by 7.5% SDS-PAGE, transferred to nitrocellulose membrane and incubated with anti-phosphotyrosine (4G10) or anti-pHER3 (21 D3). Phosphoproteins were detected with anti-mouse-POD (for 4G10) or anti-rabbit-POD (for 21D3) secondary antibodies. The membranes were stripped and reprobed with anti-HER3 antibody (sc-285).

HER3 Phosphorylation in Tissue Samples

Using a microtome, 2-4 µm thin sections were cut, mounted on silanized glass slides and dried at 60° C. for 30 minutes and at 38° C. overnight. Deparaffinisation and rehydration of the specimen was achieved by incubating 2×5 minutes in Xylol, 2×2 minutes in 100% ethanol and 2 minutes each in 96%, 80% and 70% ethanol. After rinsing 20 seconds in distilled water, the slides were incubated for two minutes in PBS. For antigen retrieval the specimens were incubated in a steamer, containing a cuvette filled with 1 mM EDTA pH 8.0 at 96-98° C. for 20 minutes. The slides were cooled down for 20 min at RT, then washed 5 minutes in A. dest. Except for incubation with primary antibody pHer3, the following steps were performed at room temperature:

Endogenous peroxidases were blocked for 20 minutes in RE7101 (3 drops per section, Novocastra). Sections were then washed 5 minutes in A. dest. and 5 minutes in TBS buffer. Unspecific background staining was blocked by incubation with 10% goat serum in PBS for 20 minutes. Solution was tapped off and sections were incubated with monoclonal antibody rabbit-anti-pHer3 (10 µg/ml Lot #3), Cell Signaling) overnight at 4° C. in a humidified chamber (1:40 in Dako dilution buffer). As IgG isotype control IgG rabbit absorbed (15 g/L, X0936 Dako) was used (1:50.000 in Dako dilution buffer). To remove the antibody, the slides were washed 2×5 minutes with TBS/TWEEN 0.05% and 1×5 minutes with TBS. Post Primary Block (RE7111, Novocastra) was added (3 drops per sections) for 30 minutes, followed by washing as before. Then NovoLink Polymer RE7112 (3 drops per section, Novocastra) were added, incubated for 30 minutes and removed in a washing step as before. Staining was achieved by incubation with 100 µl DAB-substrate-chromogen-solution for 10 minutes. In a last step, the slides were rinsed three times in fresh distilled water, counterstained with Harris' hematoxylin and covered with a glass slide.

Xenograft Experiments

The anti-tumor efficacy of a HER modulator were evaluated in human xenograft tumor studies. In these studies, human tumors were grown as xenografts in immunocompromised mice and therapeutic efficacy was measured by the degree of tumor growth inhibition in response to administrations of the HER modulator. In order to determine, whether a HER modulator, as defined in forgoing paragraphs, at least partially interferes with tumor growth of human cancer cells in vivo, cells were implanted in nude/nude or SCID mice, using protocols known to the skilled artisan (Sausville and Burger, (2006), Cancer Res. 66, 3351-3354). For example tumor cells were injected under the skin of nude mice, resulting in subcutaneous tumor growth on the back of the animals. Treatment was either started at the time of tumor cell implantation or when tumors had reached a defined size, e.g. a mean volume of 20-50 mm$^3$. Prior to first treatment, mice were randomized to assure uniform tumor volumes (mean, median and standard deviation) across treatment groups. Typical dosing regimen included weekly administrations of 25 mg/kg of the HER modulator into the interpeneum. The first treatment included a loading dose of 50 mg/kg. Mice in control arms received agents, e.g. doxorubicin (pharmaceutical grade) with known cytostatic or cytotoxic activity against the human tumor cells.

Detection of HER3 Phosphorylation in Human Patient Tissues

For the selection of patients amenable for an anti-HER3 mAb treatment, the HER3 receptor activation will be measured via IHC in cellular samples (tumor material at time of diagnosis, fresh tumor material prior to treatment, normal tissue) derived from a patient deemed to be a candidate for an anti-HER3 mAb treatment. The cellular sample will be achieved through various methods of biopsies (e.g. punch, brush, incisional, core) or other methods (e.g. plucking of hair and air follicles, buccal swab). The harvested tissue material will be processed, fixed and analyzed for presence of pHER3 (qualitative assay) and the relative amount of pHER3 (quantitative assay) via immunohistochemistry or other applicable methods (e.g. rtPCR, WB). An activation score for pHER3 will be calculated and the subject will be enrolled in the clinical study/treatment routine accordingly.

Assessment of the Efficacy of a HER3 Inhibitor

The efficacy of an anti HER3 antibody in reducing HER3 receptor activation and/or HER3 mediated signal transduction can be assessed in cellular samples derived from a subject that has been treated with said anti HER3 antibody. The cellular samples can be retrieved in the previously described way, the timing of the samples is dependent on the treatment duration, schedule and follow up of therapy, but at least 2 samples will be taken (one at treatment start and one at maximum response). The quantitative and qualitative measurements for the 2 time points will be compared and the pharmacodynamic effect will be calculated from the delta/shift of values for the HER3 receptor activation. Normal tissue (e.g. skin, hair follicles) will serve as surrogate tissue for the tumor tissue, since the normal tissue may be easier accessible for the clinical routine diagnostic.

Development of Prognostic Index for Subjects Amenable to Anti-HER3 mAb Therapy

For patients that have received an anti-HER3 mAb treatment, the outcome of the treatment will be correlated with the level of HER3 phosphorylation and the modulation of the phosphorylation/activation over time. The resulting prognostic index will be compared with standard indices (e.g. tumor grade, stage, patient demographics, treatment) and it will be determined whether pHER3 can serve as a superior marker for efficacy of the treatment, prognostic index for outcome, variabilities in response to the treatment or recurrence of the disease. Ultimately HER3 phosphorylation may become a new surrogate marker for the assessment of a rsik-benefit score or a positive/negative prognosis with respect to anti-HER3 mAb therapy and other targeted or classical antineoplastic therapies.

Clinical Study to Identify Cancer Patients for Treatment with an Anti HER3 Antibody A cellular sample comprising normal and/or cancer cells is obtained from a subject deemed eligible for the treatment. The following methods are used in routine clinical practice to retrieve a tissue sample: swab (buccal, nasal swab), cuts (finger nails, toe nails), fine needle aspiration, punch biopsy, brush biopsy, scratch biopsy, biopsy using pincers or other surgical instruments, aspiration (e.g. blood, bone marrow), puncture (e.g. ascites, pleural effusion, cerebrospinal fluid), (micro-derm) abrasive cytology, incision, surgical removal of organ parts or whole anatomical structures (bloc resection, tumor excision, lumpectomy), radiation assisted surgical procedure (gamma-knife surgery, laser assisted surgery), lavage (e.g. broncho-alveolar lavage, abdominal lavage), external drainage of organs (e.g. hydrocephalus, nephrostomy, T-drain bile duct). Any other method known in clinical practice for harvesting of tissue samples can be used as well. The biological sample is analyzed for HER3 phosphorylation, e.g., by immunoprecipitation or Western blot analysis, and/or for the presence of HER2/HER3 and/or HER3/HER4 heterodimers by any of the techniques described above.

Clinical Study to Monitor Efficacy of Treatment with a HER3 Modulator

Patients with solid tumors (e.g. lung, colorectal, breast cancer) will undergo at least 2 biopsies for the assessment of the pharmacodynamic effects of an anti-HER3 mAb treatment evaluated through changes/modulations in the HER3 phosphorylation. At study entry, patients will be stratified for the pHER3 level and at the time of maximum clinical response, a second tissue sample will be taken from the patient. The samples will be analyzed for pHER3 expression (quantitative and qualitative) and the results are correlated with other parameters and clinical outcome. A rise in pHER3 activation may be considered as progression or non-response, whereas a decrease of pHER3 may be considered response to therapy. Patients with at least a stabilization of pHER3 levels (increase ≤25% from baseline) will continue on treatment with anti-HER3 mAb therapy, patients with an increase of pHER3>25% from baseline will be considered as progressive and treatment with anti-HER3 mAb therapy will be discontinued.

The invention claimed is:

1. A method for treating patients responsive to a target specific therapy comprising an inhibitory anti-HER3 antibody, comprising
    (a) obtaining at least one sample from a subject having a tumor disease, prior to treatment with an inhibitory anti-HER3 antibody, wherein the sample is a normal hair follicle biopsy,
    (b) obtaining at least one sample from said subject having said tumor disease after treatment with the inhibitory anti-HER3 antibody, wherein the sample is a normal hair follicle biopsy,
    (c) examining the phosphorylation level of a HER3 receptor in said samples,
    (d) determining that the phosphorylation level of the HER3 receptor is reduced after treatment with the inhibitory anti-HER3 antibody as compared to the phosphorylation level of the HER3 receptor before treatment with the inhibitory anti-HER3 antibody, and
    (e) administering to the subject with said tumor disease, who has been determined in step (d) to have a reduced phosphorylation level of the HER3 receptor, a therapeutically effective amount of said inhibitory anti-HER3 antibody,
    wherein the tumor disease is selected from the group consisting of NSCLC, breast, colon, gastric, pancreas and prostate cancer, and
    wherein said inhibitory anti-HER3 antibody is selected from the group consisting of antibody U3-1287, 105.5, SGP-1, H3 90.6, 1B4C3, and 2D1 D12.

2. The method of claim 1, wherein step (c) comprises an immunohistochemical assay, flow cytometry, ELISA or a Western Blot.

3. The method of claim 1, wherein the sample is a fresh, frozen and/or preserved normal hair follicle biopsy.

4. The method of claim 1, wherein the subject is a mammal.

5. The method of claim 4, wherein the mammal is a human.

6. The method of claim 1, wherein said HER3 receptor phosphorylation level is determined using a phospho-specific antibody.

7. The method of claim 6, wherein the phospho-specific antibody is an antibody that recognizes a phosphorylated tyrosine residue in a HER3 receptor.

8. The method of claim 7, wherein the phospho-specific antibody is directed against at least one of the tyrosine residues Y1289 or Y1222 in a human HER3 receptor.

9. The method of claim 6, wherein said phospho-specific antibody is at least one of the phospho-specific antibodies 21D3 or 50C2.

* * * * *